(12) United States Patent
Syassen

(10) Patent No.: US 9,182,299 B2
(45) Date of Patent: Nov. 10, 2015

(54) METHOD FOR THE DETECTION OF A POSSIBLE JOINT DEFECT IN A FRICTION STIR WELD SEAM

(75) Inventor: Freerk Syassen, Stadland (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 654 days.

(21) Appl. No.: 13/479,423

(22) Filed: May 24, 2012

(65) Prior Publication Data

US 2013/0135460 A1     May 30, 2013

Related U.S. Application Data

(60) Provisional application No. 61/490,605, filed on May 27, 2011.

(30) Foreign Application Priority Data

May 27, 2011  (DE) .................. 10 2011 076 631

(51) Int. Cl.
| | | |
|---|---|---|
| *G01L 1/00* | (2006.01) | |
| *G06T 7/00* | (2006.01) | |
| *G01N 21/91* | (2006.01) | |
| *G01B 11/16* | (2006.01) | |
| *G01N 21/95* | (2006.01) | |
| *G01N 3/08* | (2006.01) | |
| *G01N 21/88* | (2006.01) | |

(52) U.S. Cl.
CPC ................ *G01L 1/00* (2013.01); *G01B 11/162* (2013.01); *G01N 3/08* (2013.01); *G01N 21/91* (2013.01); *G01N 21/95* (2013.01); *G06T 7/001* (2013.01); *G01N 2021/8829* (2013.01); *G01N 2203/0296* (2013.01)

(58) Field of Classification Search
CPC .............. G01N 27/9013; G01N 27/82; G01N 27/9033; G01N 27/904; G01N 21/95; G01N 2203/0296; G01N 21/91; G01N 3/08; G01N 2021/8829; G01N 3/20; B23K 20/122; B23K 20/128; B23K 2203/10; B23K 31/12; B23K 31/125; G01B 11/162; G01L 1/00; G06T 7/001; G06T 7/0002
USPC .............. 324/238, 240; 348/125, 129; 73/760
See application file for complete search history.

(56) References Cited

U.S. PATENT DOCUMENTS

| | | | | |
|---|---|---|---|---|
| 4,893,944 | A | * | 1/1990 | Leroux ........................... 374/46 |
| 5,587,537 | A | * | 12/1996 | Simmons ................. 73/862.392 |
| 5,920,017 | A | * | 7/1999 | Pechersky ....................... 73/762 |
| 7,771,777 | B2 | * | 8/2010 | Harris et al. .................... 427/10 |
| 7,874,217 | B2 | * | 1/2011 | Carson ........................... 73/850 |
| 8,294,065 | B2 | * | 10/2012 | Mizumoto et al. ....... 219/145.22 |

(Continued)

FOREIGN PATENT DOCUMENTS

| | | |
|---|---|---|
| DE | 9115624 U1 | 2/1992 |
| DE | 102008046692 A1 | 3/2010 |

*Primary Examiner* — Sath V Perungavoor
*Assistant Examiner* — Nathnael Aynalem
(74) *Attorney, Agent, or Firm* — Carter, DeLuca, Farrell & Schmidt, LLP

(57) ABSTRACT

The disclosure provides methods for the detection of a possible joint defect, in particular a root fusion defect, in a friction stir weld seam, wherein two members are joined together and the methods include generating of a tensile stress in the region of the friction stir weld seam in the elastic range, and testing in at least some regions of a lower face of the friction stir weld seam, in order to detect any joint defect.

13 Claims, 1 Drawing Sheet

(56) References Cited

U.S. PATENT DOCUMENTS

| | | | |
|---|---|---|---|
| 2003/0164700 A1* | 9/2003 | Goldfine et al. | 324/235 |
| 2006/0108394 A1* | 5/2006 | Okaniwa et al. | 228/101 |
| 2008/0069451 A1* | 3/2008 | Ikeda | 382/199 |
| 2011/0136239 A1* | 6/2011 | Hehn et al. | 436/6 |

* cited by examiner

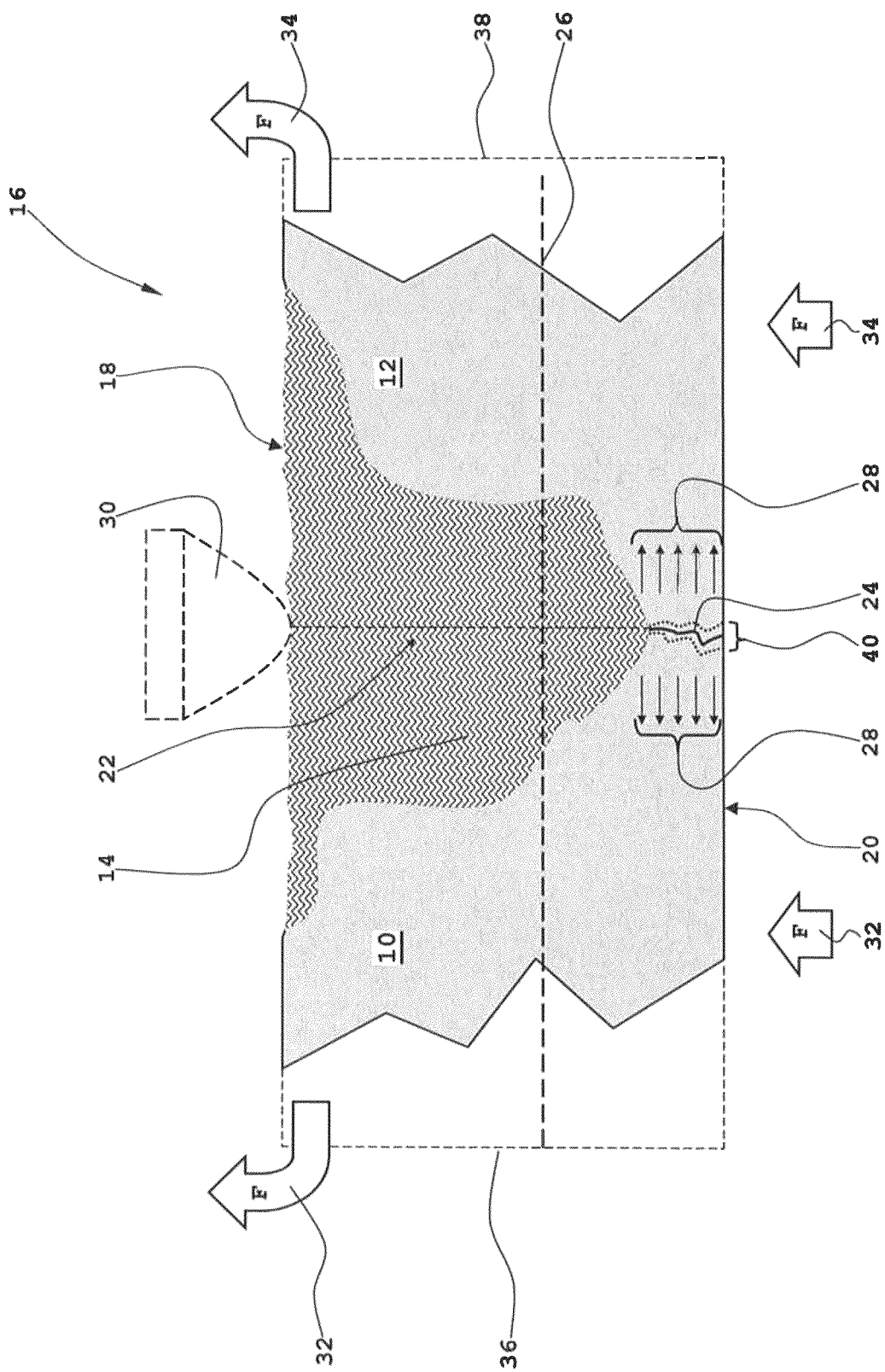

METHOD FOR THE DETECTION OF A POSSIBLE JOINT DEFECT IN A FRICTION STIR WELD SEAM

TECHNICAL FIELD

The invention concerns a method for the detection of a possible joint defect, in particular a root fusion defect, in a friction stir weld seam, by means of which two members are joined together.

BACKGROUND OF RELATED ART

Members that are joined together by means of the friction stir welding method (FSW) have an almost ideal microstructure structure in the seam region, which to a large extent can be compared with the original material properties of the initial members. By this means the strengths that can be achieved of a joint seam manufactured by means of the friction stir welding method can be almost comparable with those of the solid material. The friction stir welding method is primarily suitable for metals or metal alloys that do not have too high a melting point, such as aluminium, for example. By this means it is possible to form a butt joint between plate-type members with a material thickness of 30 mm and more.

In the friction stir welding process a rotating hard metal welding nib, which has a shoulder in an upper section, is in general introduced into the butt joint, i.e. into what is subsequently the seam formation region between the two members that are to be joined together. The friction heat generated plasticises the metal in the butt joint region and enables firstly the introduction of the rotating welding nib and subsequently its ongoing movement along the joint to form the friction stir welding seam. The shoulder of the welding nib primarily has the task of heating the material by frictional heat, and by this means softening it, while the rotating welding nib stirs the plasticised material in the weld formation region, as a result of which an intimate connection ensues between the members to be joined. The feed of the welding nib requires relatively high forces, so that the members to be joined are arranged on a workpiece support, and must be securely clamped to the latter. In a region underneath the joint, i.e. the seam formation region, extends a strip-type backing, which in the event of wear can easily be replaced, (a so-called easily replaceable backing); this in turn rests against the workpiece support. This backing extends over the whole length of the joint, and moreover slightly beyond the joint at both ends.

The distance of the end of the welding nib from the backing is an important factor in the quality of a friction stir weld seam. If this distance is too small the result can be increased wear and/or total failure of the welding nib as a result of fracture, wherein the backing can also be damaged. If, on the other hand, the distance is too large, the material is not completely plasticised and stirred by the welding nib, with the result that in the rear region, i.e. on the lower face of the weld seam, the members are not fully welded through the thickness. Such a seam in which the weld does not penetrate fully through the thickness represents one or a plurality of so-called root fusion defects (or lack of penetration=LOP); in particular in the event of dynamic loading of the weld seam these are to be viewed as notches that can lead to cracks and thus to a total failure of the member. Deployment of friction stir welded components that have not been tested is therefore impermissible in sectors in which safety is relevant, such as, for example, in aviation or in power station technology.

A major problem consists in being able to detect such root fusion defects reliably, since the lower face of the friction stir weld seam, in particular as a result of the use of the backing, and the metal fused on in the weld formation region, has a very smooth surface and the members, even in the region of the root fusion defects, are still "cold welded", i.e. for practical purposes are "adhesively" cemented together, or are "interlocked" together, so that in general no cracks occur that can be detected in a straightforward manner. Nevertheless, as a result of the edges of the joint in the region of the root fusion defects that are just "cold welded" together, only a very low mechanical strength is provided in comparison to that of a zero-defect friction stir weld seam; this strength does not even begin to approach the load capacity of the initial members.

SUMMARY

The object of the invention is therefore to specify a method with which any root fusion defects in a friction stir weld seam between two members can be reliably, completely and quickly detected.

This object is achieved by means of a method in accordance with claim 1, which comprises the following steps:
a) Generation of a tensile stress in the vicinity of the friction stir weld seam in the elastic range, and
b) Testing in at least some regions of a lower face of the friction stir weld seam, in order to detect any joint defect.

The tensile stress induced in step a) into the friction stir weld seam between the joined members serves to open up, or to bend open, any joint defect in the form of a "cold welded" crack in the region of a lower face of the seam. Here the tensile stress is generated by means of external mechanical forces applied to the joined members; these forces lead to a slight deformation of the joined members. The mechanical forces hereby engage with the joined members such that a tensile stress of suitable magnitude is always formed underneath the neutral axis. The magnitude of the tensile stress is here dimensioned such that the elastic limit of the metal, or metal alloy, deployed for each of the members, is not exceeded. The testing of the lower face of the seam in step b) is undertaken with a multiplicity of different testing methods. Here reference can be made, for example, to dye penetration testing, the "pattern comparison method", or shearography.

In accordance with an advantageous development of the method provision is made that before step a) a penetrating dye is applied to the lower face of the friction stir weld seam, and testing is undertaken in step b) by means of a dye penetration test.

In the so-called dye penetration test the penetrating dye, in accordance with one variant of the method, is applied onto the lower face of the friction stir weld seam in a tensile stress-free state in the region to be tested. This is undertaken in an additional step of the method before step a). The application of dye can be undertaken over the full surface, or only in some regions, depending upon the extent of the test. A tensile stress is them applied to the weld seam in step a). As a consequence of the opening or spreading of the "cold welded" cracks that is hereby caused in the region of any joint defect, the dye, at least partially, penetrates into the latter. After the joined members have been restored to the stress-free state, the penetrating dye squeezes out from the region of the joint defect, in particular a root fusion defect, and is amenable to direct visual detection in the course of the dye penetration test in step b). The testing for the presence of possible joint defects in step b) can, in a deviation from the above in one variant of the method, also be undertaken in the ongoing presence of the tensile stress, i.e. the joined members are not restored to the stress-free state before the test. The dye application can take place in all set-ups either before or after the generation of the tensile stress, since the penetrating dye possesses high penetrability and penetrates into the finest cracks or capillaries.

A measured image of the penetrating dye that has squeezed out is preferably taken by means of a CCD digital camera and stored in a computer. The one or more measured images can subsequently be evaluated by means of suitable image evaluation software installed on the computer, so as to locate exactly the positions of any joint defects within the friction stir weld seam and to document them. In particular in the case of longer friction stir weld seams, and a test region that is designed to extend over the whole length of the seam, it is necessary to produce a multiplicity of images, and reference images, so as to be able to test the complete profile of the seam. The individual images can be joined together digitally by means of suitable software (so-called "stitching" software), and with utilisation of the computer as necessary can be combined into a large image file that can be evaluated in a homogeneous manner. Furthermore it can be advantageous for purposes of simplification of the actual test, directly after the application of the penetrating dye—before the application of the tensile stress in step b)—in a further step, inserted in between, to produce at least one reference image of the lower face of the friction stir weld seam coated with the penetrating dye, which then in the course of the testing in step b) is compared with the measured image that documents the dye that has squeezed out.

In a further variant of the method provision is made that before step a) a pattern, in particular a primer with an irregular pattern of points applied on it, is applied to at least some regions of the lower face of the friction stir weld seam, and a reference image is taken of the pattern, and after step a) a measured image is taken of the pattern, wherein the testing in step b) takes the form of a comparison of the measured image with the reference image.

In the course of the method that is deployed in this variant, here in accordance with definition designated as the "pattern comparison method", an irregular pattern of points is applied, for example, to the lower face of the friction stir weld seam in the test region of interest. The pattern of points consists of a multiplicity of points with differing diameters, wherein the distances between the points also vary in a likewise random manner. The pattern of points can be applied, for example, by means of a "splattering" spray gun. For purposes of increasing the contrast a bright primer can first be applied, onto which the pattern of points is subsequently sprayed. In a variation the pattern can also have other geometric structures, such as, for example, ellipses or lines. For purposes of executing the seam test by means of the "pattern comparison method" a reference image is taken of the lower face of the seam, i.e. of the applied pattern in a tensile stress-free state, and at least one measured image is taken with the tensile stress applied, The reference image and the measured image are once again preferably taken with a CCD digital camera and stored in the computer. The evaluation for the detection of any joint defects is undertaken by means of specialised image evaluation software, which can detect and evaluate even slight structural alterations in the pattern of points—such as, for example, slight displacements in the positions of the points in relation to one another.

In a further variant of the method a reference image of the lower face of the friction stir weld seam is taken before step a) by means of shearography, and after step a) a measured image of the lower face of the friction stir weld seam is taken by means of shearography, wherein the testing in step b) takes the form of a comparison of the measured image with the reference image.

The shearography method applied for purposes of testing in step b) is suitable for non-contact detection of mechanical defect locations in a multiplicity of members. The method records the gradient of the deformation in the seam region, which is essentially brought about by the tensile stress that is acting on the seam. In shearography the region of the lower face of the seam to be tested is illuminated with a widened laser beam. The reflected laser radiation passes through an optical "shear element, i.e. displacement element" and is then evaluated, for example, by means of a conventional CCD digital camera. By means of the "shear element", which can, for example, take the form of an optical wedge, two images of the seam region to be tested, slightly displaced from one another, appear in the image plane of the CCD digital camera; these are overlaid on one another to form an interference image.

For purposes of executing the seam test by means of the shearography method in step b) a reference image is firstly taken by means of the CCD digital camera under laser light in the unloaded state of the seam, and a measured image is then taken of the seam subjected to tensile stress; these images are stored in the computer for further processing. The difference between the reference image in the unloaded state (free of tensile stress) and the actual measured image in the loaded state contains all the information concerning any deformations on the lower face of the seam caused by the tensile stress; such deformations provide clear evidence of the presence of joint defects. Thus the evaluation can take place in terms of a computer-generated difference image between the reference image and the measured image by means of suitable image evaluation software that has been adapted for this purpose.

In accordance with a further variant of embodiment of the method provision is made that after step a) a measured image of the lower face of the friction stir weld seam is taken by means of shearography, wherein the testing in step b) takes place in terms of a direct evaluation of the measured image.

This variant of the method makes use of an absolute measurement that does not require a previous reference image.

Non-homogeneous structures, i.e. in particular structures that behave in an uneven manner, in the image measured using shearography of the friction stir weld seam when subjected to tensile stress, provide direct evidence on their own account of the presence of a joint defect, in particular a critical root fusion defect.

In an advantageous development of the method provision is made that the tensile stress is generated by bending the joined members over an edge, wherein the edge is arranged in the region of an upper face of the friction stir weld seam, and the edge rests against at least some regions of the latter.

As a consequence of the edge arranged as an abutment in the region of the upper face of the friction stir weld seam, it is possible to generate tensile stresses of an accurately defined magnitude within the friction stir weld seam by simply bending the free member edges upwards.

In accordance with a further embodiment of the method the tensile stress is generated by means of a reduced pressure $p_u$ in the region of the lower face of the friction stir weld seam.

As a consequence of this configuration no free access is required to the member edges of the joined members for purposes of generating the tensile stress.

In a further advantageous development of the method provision is made that the tensile stress is generated by bending two outer member edges upwards in the same direction.

In this set-up no (bending) edge is required as an abutment for the joined members. Here the opposing member edges of the joined members are bent upwards in the same direction, at the same time and with the same deployment of force, so as to generate a tensile stress in the friction stir weld seam in the region underneath the neutral axis that is as homogeneous as possible. In all variants in which a tensile stress is generated the elastic limit of the materials deployed in each of the members is not exceeded, i.e. no permanent plastic deformation of the joined members occurs as a result of the action of the tensile stress in the seam region underneath the neutral axis.

BRIEF DESCRIPTION OF THE DRAWINGS

An embodiment of the invention will now be explained in more detail with reference to the appended FIG. 1 which shows a schematic cross-sectional representation through two members joined together by means of a friction stir weld seam, with a joint defect that is to be detected in the form of a root fusion defect (a so-called "LOP").

DETAILED DESCRIPTION

FIG. 1 shows two members 10, 12, which are joined together by means of a friction stir weld seam 14 to form a superordinate design component 16, such as, for example, a fuselage shell of an aircraft. The members 10, 12 are as a rule formed with a comparatively low melting point metallic material, such as for example aluminium, or an aluminium alloy, which is suitable for the friction stir welding process of known art.

In the region of an upper face 18 of the friction stir weld seam 14 the members 10, 12 are completely welded together, whereas in the region of a lower face 20 of the members 10, 12 in a butt joint region 22 they are not completely welded through, and a so-called root fusion defect 24 is formed. In the region of the root fusion defect 24 the inner member edges, not designated are just "cold welded"; these edges are only "adhesively" cemented with one another, or are interlocked with one another. Accordingly only a low mechanical load capacity is provided in this zone. By virtue of the high notch effect of the root fusion defect 24 a total failure of the friction stir weld seam 14 can occur even at low loads, that is to say, the result can be a fracture of the complete friction welded component 16. In the state of the component 16 as shown the root fusion defect 24 can only be detected with great difficulty; by virtue of the smooth backing deployed in friction stir welding and the material of the members 10, 12 that is plasticised in this region the lower face 20 of the friction stir weld seam 14 is almost completely plane, and by virtue of the "cold welded" member edges the root fusion defect 24 is not disclosed as a crack.

In order nevertheless to enable detection of a possible root fusion defect 24 using a method that is as reliable as possible, it is recommended in accordance with the inventive method in step a) to induce into the component 16 a mechanical tensile stress 28 underneath a horizontal neutral axis 26, that is to say, in the region of the lower face 20 of the friction stir weld seam 14, i.e. in the region of a potential root fusion defect 24. The magnitude of the tensile stress 28 is dimensioned such that only elastic deformation occurs in the region of the friction stir weld seam 14, and any permanent plastic deformation is ruled out. Here the tensile stress is maintained constant at least with respect to time during step b), in which the actual testing takes place.

The generation of the tensile stress 28 can, for example, be undertaken by bending the component 16, i.e. the members 10, 12 welded to one another, over an edge 30, wherein the edge 30 is preferably brought into contact with the region of the upper face 18 of the friction stir weld seam 14, at least in some regions. The tensile stress 28 necessary for purposes of testing the friction stir weld seam 14 is in this case built up by bending forces 32, 34 of the same magnitude, acting symmetrically on the lower face on both sides of the butt joint region 22 and directed upwards. Alternatively the bending forces 32, 34 can also act laterally on the outer member edges 36, 38, in order to generate the tensile stress 28 required by the method, so that the edge 30 is not required. Apart from this it is possible to replace the required bending forces 32, 34 by the application of a reduced pressure $p_u$ by means of a vacuum pump, not indicated, in the region of the lower face 20 of the friction stir weld seam 14. In this case the outer member edges 36, 38 must be fixed in their spatial location, i.e. they must in particular be clamped sufficiently securely. This procedure has the particular advantage that no free access is required to the upper face 18 of the friction stir weld seam 14. At least two of the three variants that are here described in just an exemplary manner can also be combined with one another for purposes of generating the tensile stress 28. By virtue of the tensile stress 28—as shown in FIG. 1—any root fusion defect 24 is opened out into a microscopically small crack 40, i.e. the "cold welded" inner member edges in the butt joint region 22 underneath the neutral axis 26, i.e. in the region of the lower face 20 of the friction stir weld seam 14, are detached from one another, i.e. are pulled apart from one another, as a result of which the detection of any root fusion defect by means of testing procedures of known art is significantly simplified—or perhaps made possible for the first time. The tensile stress 28 always builds up underneath the neutral axis 26, that is to say in the region of the lower face 20 of the friction stir weld seam 14 with the possible root fusion defect 24. Apart from this no kind of permanent deformation of the component 16 occurs.

Only in step b) is the actual testing of the friction stir weld seam 14 for joint defects undertaken, in particular with regard to the root fusion defect 24 with the fine (hairline) crack 40 as a result of the action of the tensile stress 28. For purposes of detecting a possible root fusion defect 24 the testing methods cited in the introduction are preferably applied.

If the testing for the presence of a root fusion defect 24 is undertaken with the aid of the dye penetration test, then, in a step inserted before step a), the lower face 20 of the friction stir weld seam 14 is firstly coated with a suitable dye, which remains in a fluid state over the whole time period of the test. Then in step a) the tensile stress 28 is built up and held constant over a sufficiently long time period, as a result of which the penetrating dye, by virtue of capillary forces amongst other mechanisms, seeps into the fine crack 40 of the root fusion defect 24 that opens out as a result of the action of the tensile stress 28. The duration of the action of the tensile stress 28 must be dimensioned such that a sufficient quantity of the penetrating dye can penetrate into any such crack 40. In some circumstances a modulation over time of the magnitude of the tensile stress 28 is advantageous, so as to support the seeping of the penetrating dye into the base of the crack 40 by means of a "pumping action" of the crack 40 that is hereby caused. In step b) the members 10, 12 are then moved back into the stress-free (initial) state, as a result of which the crack 40 that was formed in the region of any root fusion defect 24 is at least partially closed once again, and the penetrating dye that migrated into the crack 40 is at least partially squeezed out or pushed out of the latter once again. By means of an imaging method the penetrating dye that has squeezed out and thus the crack 40 of the root fusion defect 24 can be directly detected in a simple manner.

For example, at least one measured image is taken with the aid of a CCD digital camera of the lower face 20 of the friction stir weld seam 14 with the penetrating dye that has squeezed out, and this is stored in a computer. On the computer is installed image evaluation software that is suitable for the respective testing method that is used in step b). The detection of any joint defect is then undertaken by means of the image evaluation software, which in this case is able to detect the penetrating dye that has squeezed out, and moreover is able to determine accurately its position along the lower face 20 of the friction stir weld seam 14. For purposes of simplifying the evaluation by means of the image evaluation software a reference image can, if required, be taken of the lower face 20 of the friction stir weld seam with the penetrating dye coated on in a tensile stress-free state; in step b) this is then compared with the actual measured image, which shows the penetrating dye that has emerged. In an alternative form of the method it is possible to apply the penetrating dye onto the lower face 20 of the friction stir weld seam 14 only after the generation of the tensile stress 28 in step a).

In a further variant of the method the testing method here designated by the term "pattern comparison method" is deployed. In this method the region of the lower surface 20 of the friction stir weld seam 14 to be investigated is firstly coated with a primer, i.e. preferably with a bright and matt colour for purposes of increasing contrast and also minimising undesirable light reflections. An irregular pattern of points then is applied onto the primer. Instead of a pattern of points other arbitrary geometric structures can also be applied onto the primer. In the case of a darker lower face 20 of the friction stir weld seam 14 that only reflects a small amount of light the application of a primer can be dispensed with under some circumstances. In two steps positioned before step a) the primer is firstly applied with the irregular pattern of points in the stress-free state of the members 10, 12, at least one reference image is produced of this pattern, and the reference image is stored in the computer. In step a) the tensile stress 28 is then built up and held constant for as long as necessary until in the following step b) at least one measured image has been taken by means of the CCD digital camera of the lower face 20 of the friction stir weld seam 14 subjected to the tensile stress 28, and has been stored in the computer. The detection of a possible root fusion defect 24 is undertaken once again by means of a comparison between the at least one reference image and the at least one measured image within the computer with the aid of image evaluation software that is suitable for this purpose. For example, the image evaluation software can determine any displacements of points within the pattern of points relative to one another, for example as a result of the crack 40 of the root fusion defect 24 that has occurred as a result of the tensile stress 28, and can establish and display the latter's exact position in the friction stir weld seam 14.

In a further alternative form of the method the testing for the presence of a root fusion defect 24 can be undertaken by means of shearography as elucidated in the introduction. In this variant of the method in a step positioned before step a) at least one shearography reference image is taken by means of the CCD camera of the lower face 20 of the friction stir weld seam 14, i.e. of the testing region of interest, in the tensile stress-free state. In step a) the tensile stress 28 is applied and held constant for at least the duration of the test. In step b) at least one measured image is then taken with a CCD digital camera with the aid of shearography of at least a part of the lower face 20 of the friction stir weld seam 14, and stored in the computer. Afterwards the members 10, 12 can be moved back into the stress-free state. The detection of a possible root fusion defect 24 is undertaken in terms of a comparison of the at least one reference image with the at least one measured image with the aid of suitable image evaluation software running on the computer.

In a further variant of the method the prior production of the at least one reference image is dispensed with. The detection of a possible root fusion defect 24 is undertaken solely on the basis of the at least one measured image of the friction stir weld seam 14 underneath the neutral axis 26 subjected to the tensile stress 28. If a root fusion defect 24 is present non-homogeneous geometric structures in a measured image generated by means of shearography, in themselves point in general to the presence of a deformation, even if only a slight deformation, in the region of the lower face 20 of the friction stir weld seam 14 and thus to a crack 40 of a root fusion defect 24 that has been opened out by the tensile stress 28.

The inventive testing method allows for a secure process of detection of a root fusion defect 24, in the region of a lower face of a friction stir weld seam 14 between two members 10, 12, that is quick, reliable, and easy to manipulate, wherein false indications are reliably ruled out.

The invention claimed is:

1. A method for the detection of a possible joint defect in a friction stir weld seam, by means of which two members are joined together, each member of the two members being made of material, the method comprising:
   a) generating a tensile stress below an elastic limit of the materials of each member in the region of the friction stir weld seam to bend open any joint defect;
   b) testing in at least some regions of a lower face of the friction stir weld seam, in order to detect any joint defect; and
   c) before step a):
      applying a pattern to at least some regions of the lower face of the friction weld seam, and
      taking a reference image from the pattern, wherein the pattern includes a primer with an irregular pattern of points applied to it.

2. The method in accordance with claim 1, further comprising:
   before step a) applying a penetrating dye to the lower face of the friction stir weld seam.

3. The method in accordance with claim 2, wherein the testing step includes a dye penetration test.

4. The method in accordance with claim 1, further comprising:
   after step a) taking a measured image of the pattern.

5. The method in accordance with claim 4, wherein the testing step includes a comparison of the measured image with the reference image.

6. The method in accordance with claim 1, further comprising:
   before step a) taking a reference image of the lower face of the friction stir weld seam by shearography.

7. The method in accordance with claim 6, further comprising:
   after step a) obtaining a measured image of the lower face of the friction stir weld seam by shearography.

8. The method in accordance with claim 7, wherein the testing step includes a comparison of the measured image with the reference image.

9. The method in accordance with claim 1, further comprising:
   after step a) obtaining a measured image of the lower face of the friction stir weld seam by shearography.

10. The method in accordance with claim 9, wherein the testing step includes a direct visual evaluation of the measured image.

11. The method in accordance with claim 1, wherein the generating step includes generating by bending the joined members over an edge, wherein the edge is arranged in a region of an upper face of the friction stir weld seam, and the edge rests against at least some regions of the latter.

12. The method in accordance with claim 1, wherein the generating step includes generating a negative pressure $p_u$ in the region of the lower face of the friction stir weld seam.

13. The method in accordance with claim 1, wherein the generating step includes generating by bending two outer member edges upwards in the same direction.

* * * * *